(12) United States Patent
Baan et al.

(10) Patent No.: US 7,823,452 B2
(45) Date of Patent: Nov. 2, 2010

(54) SLIP RING POSITIVE Z FORCE LIQUID ISOLATION FIXTURE PERMITTING ZERO NET FORCE ON WORKPIECE

(75) Inventors: Robert L. Baan, Wallkill, NY (US); Carla A. Bailey, Poughkeepsie, NY (US); Vladimir Jambrih, Kingston, NY (US); Robert P. Katz, Lagrangeville, NY (US)

(73) Assignee: International Business Machines Corporation, Armonk, NY (US)

( * ) Notice: Subject to any disclaimer, the term of this patent is extended or adjusted under 35 U.S.C. 154(b) by 456 days.

(21) Appl. No.: 11/862,540

(22) Filed: Sep. 27, 2007

(65) Prior Publication Data

US 2009/0084183 A1 Apr. 2, 2009

(51) Int. Cl.
*G01N 29/04* (2006.01)
(52) U.S. Cl. .......................................... 73/606; 73/618
(58) Field of Classification Search .................... 73/606, 73/617–621, 627–629, 612–614, 633–634
See application file for complete search history.

(56) References Cited

U.S. PATENT DOCUMENTS

| 3,506,887 | A | * | 4/1970 | Gutteridge | ................... 257/296 |
|---|---|---|---|---|---|
| 4,294,454 | A | | 10/1981 | Cannings | |
| 4,932,358 | A | | 6/1990 | Studley | |
| 5,046,363 | A | * | 9/1991 | Moore | ........................ 73/588 |
| 5,421,401 | A | | 6/1995 | Sherstinsky | |
| 5,660,699 | A | | 8/1997 | Saito | |
| 5,833,820 | A | | 11/1998 | Dubin | |
| 6,244,936 | B1 | | 6/2001 | Kao | |
| 6,523,426 | B1 | | 2/2003 | Vincent | |
| 6,569,302 | B1 | | 5/2003 | Steinrucke | |
| 7,395,698 | B2 | * | 7/2008 | Degertekin | ................... 73/105 |
| 2008/0022774 | A1 | * | 1/2008 | Lu | .............................. 73/606 |

* cited by examiner

*Primary Examiner*—Helen C. Kwok
(74) *Attorney, Agent, or Firm*—Graham V. Jones; Yuanmin Cai

(57) ABSTRACT

Apparatus for Scanning Acoustic Microscopy (SAM) of a semiconductor device including a substrate with an acoustic probe, The substrate has upper and lower surfaces. A sealed lower space provides an environment surrounding the lower surface. An upper ring structure formed above the upper surface includes an upper sealing ring in contact with the upper surface, with the upper sealing structure and the seal forming a dam for retaining the acoustic transmission fluid above the upper surface. A fixture base retains a lower sealing ring in contact with the lower surface surrounding the lower surface. An acoustic scanning probe positioned confronting the upper surface of the semiconductor device extending into the acoustic transmission fluid retained in contact with the upper surface.

20 Claims, 5 Drawing Sheets

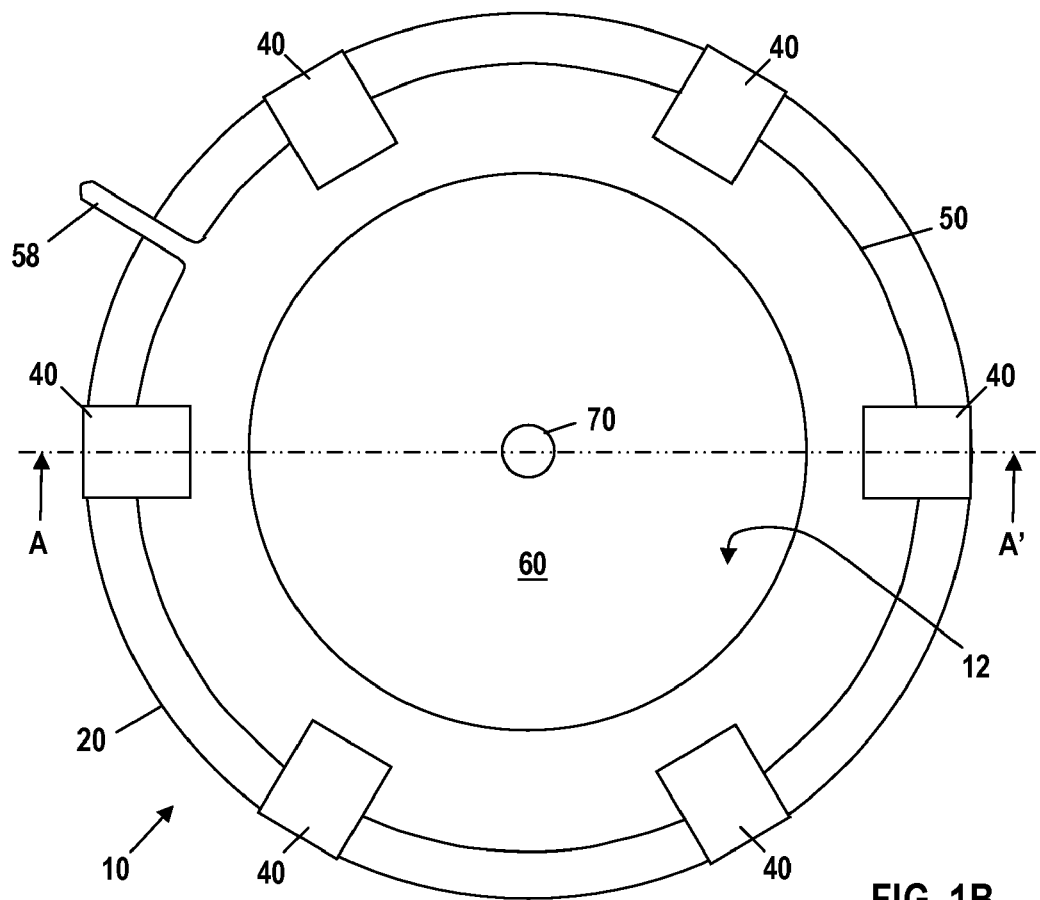
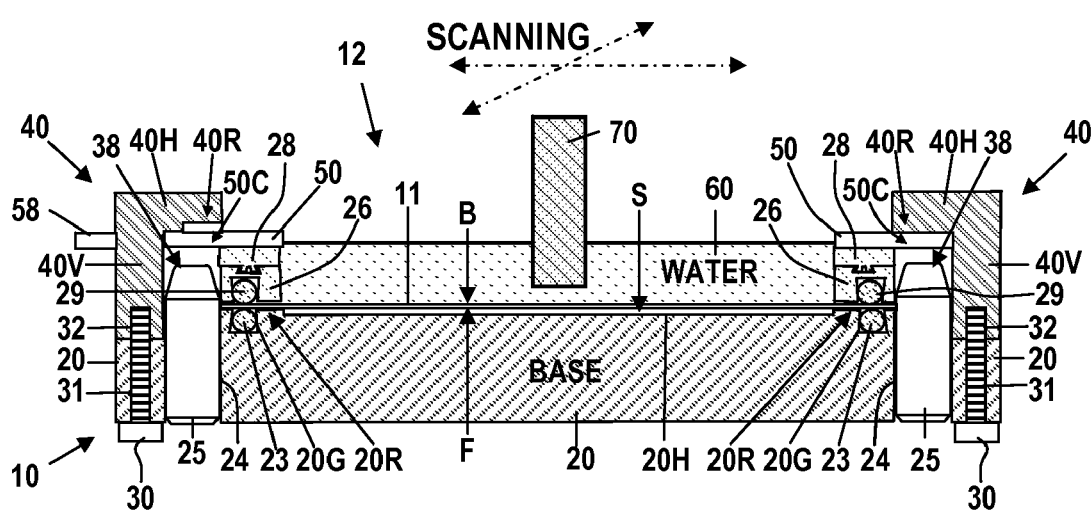

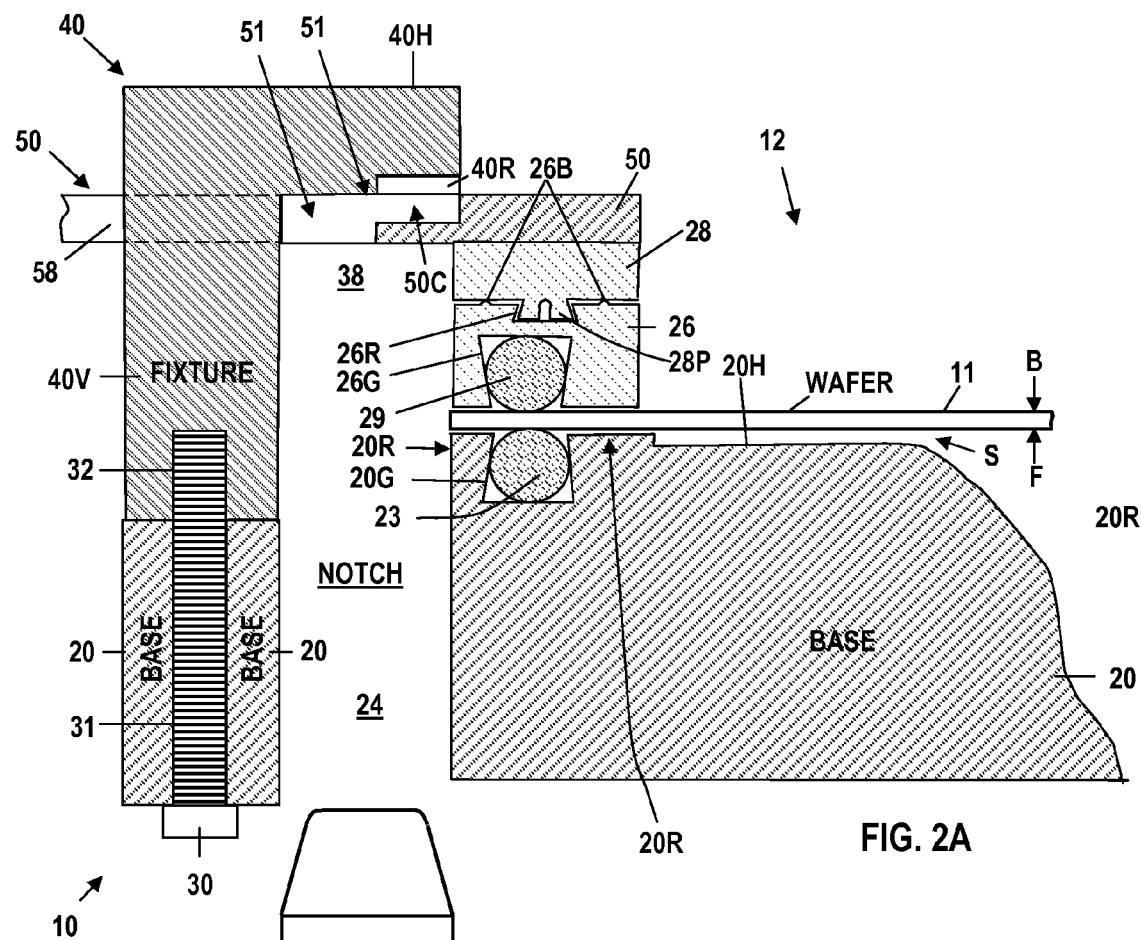

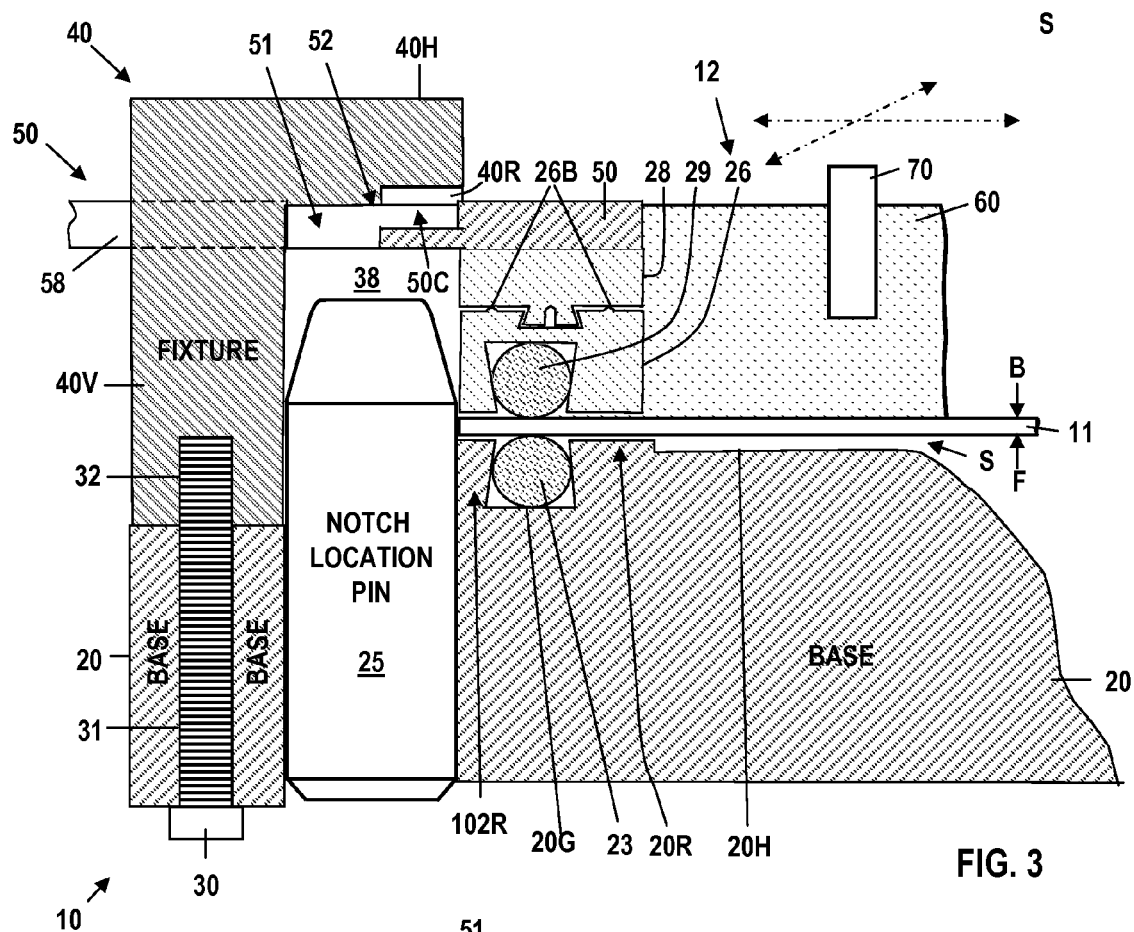
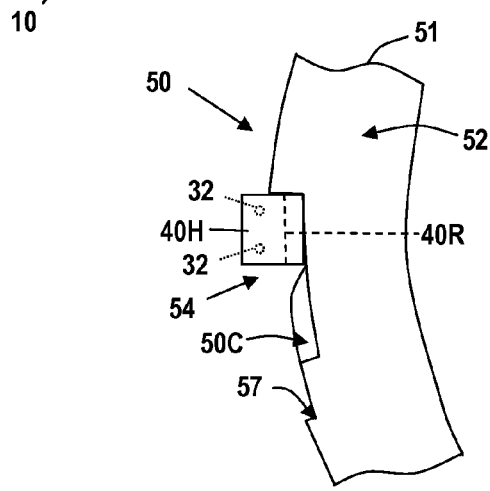 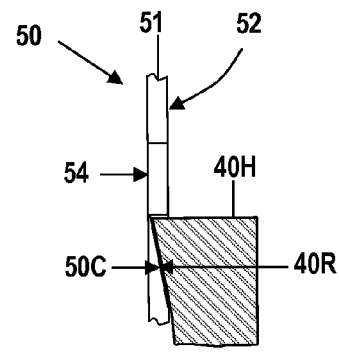
FIG. 3
FIG. 7A    FIG. 7B

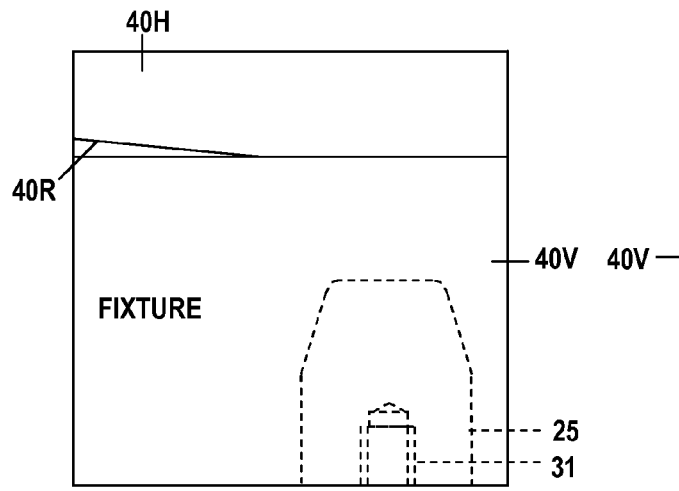
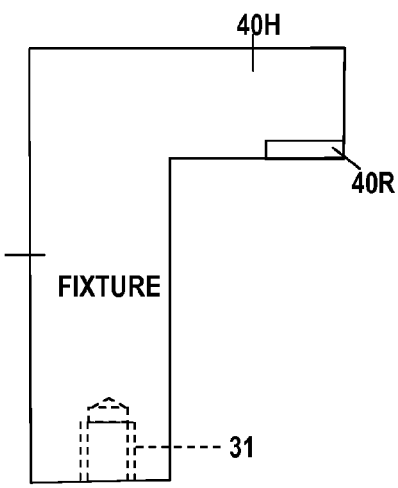
FIG. 4A
FIG. 4B
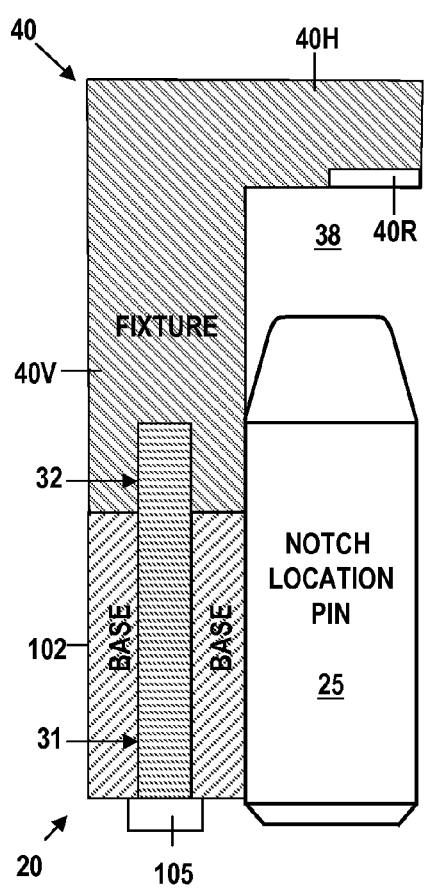
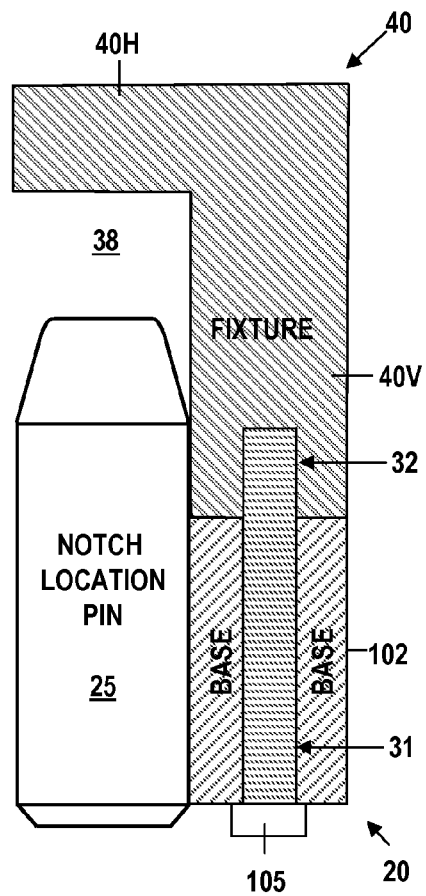
FIG. 5A
FIG. 5B

SLIP RING POSITIVE Z FORCE LIQUID ISOLATION FIXTURE PERMITTING ZERO NET FORCE ON WORKPIECE

CROSS-REFERENCE TO RELATED APPLICATION

This application contains subject matter which is related to the subject matter of the copending, commonly assigned, abandoned U.S. patent application Ser. No. 11/495,243 of Minhua Lu entitled "Imaging Thin Film Structures by Scanning Acoustic Microscopy," published as U.S. Patent Application Publication 2009/0022774, which is assigned to the same assignee as this application, International Business Machines Corporation of Armonk, N.Y. The subject matter of the above patent application is hereby incorporated herein by reference in its entirety.

BACKGROUND OF THE INVENTION

This invention relates to fixtures employed in testing features on a first surface of a device under test, which has an opposite surface; and more particularly to means for isolating the opposite surface of a semiconductor device under test from fluids retained in contact with the first surface.

In the past, measurement of features of Devices Under Test (DUT)s by Scanning Acoustic Microscopy (SAM) and C-mode Scanning Acoustic Microscopy (C-SAM) has been performed by immersion of a workpiece in an amplification medium comprising an acoustic transmission fluid, e.g. alcohol, oil, or water, to transmit the sound waves necessary for the measurement. Copending, commonly assigned U.S. patent application Ser. No. 11/495,243 of Lu entitled "Imaging Thin Film Structures by Scanning Acoustic Microscopy" describes C-SAM testing apparatus used for testing devices with one side exposed to an acoustic transmission fluid, e.g. water, and the other side isolated from the transmission fluid in a space filled with air. In the past, testing with C-SAM apparatus has involved complete immersion of the workpiece in an amplification medium (alcohol, oil, water) to transmit the sound waves necessary for the measurement.

Whereas an acoustic transmission fluid is preferred as a transmitter of acoustic waves, there is a problem that the acoustic transmission fluid should not be in contact with the front surface of a DUT. The solution described by the Lu application is to immerse the back surface of the DUT and to isolate the features on the front surface of the DUT by employing an impervious barrier structure. The impervious barrier structure retains the acoustic transmission fluid in contact with the back surface of the DUT. The barrier excludes the acoustic transmission fluid from the front surface of the DUT. That is to say that the front surface of the DUT is located in a vacuum or in a gas and is isolated from the acoustic transmission fluid, either by providing a sealed chamber protecting the front surface, or by providing a dam, while the acoustic transmission fluid is retained in contact with the back surface of the DUT.

U.S. Pat. No. 4,932,358 of Studley et al entitled "Perimeter Wafer Seal" presses a seal ring (preferably composed of monel metal) against a wafer on a CVD chuck around the outer periphery of the wafer with sufficient force to hold the backside of the wafer against the chuck. Thus no CVD material may deposit on the backside of the wafer. The seal ring has one surface for contacting the front side of the wafer and a second surface that extends close to the CVD chuck, so the edge of the wafer is protected from CVD coating. Thus CVD coating is confined to the front side of a wafer. In a preferred embodiment, an apparatus with a slide operated by a cam lever and a tension spring moves the seal ring and presses it against a wafer with multiple chucks attached to a rotatable turret within a CVD chamber.

U.S. Pat. No. 5,421,401 of Sherstinsky et al. entitled "Compound Clamp Ring for Semiconductor Wafers" uses a compound clamp ring to secure a semiconductor wafer to a wafer pedestal during wafer processing to prevent leakage of coolant gases circulated at the backside of the wafer into the process environment. The clamp ring seals against application of back side gas pressure against wafers to ensure thermal transfer during plasma processing, but it does not provide a wet fluidic seal, nor does it offset Z-forces against a wafer at points of wafer seal contact, and it expressly avoids the use of elastomers because of possible outgassing in a vacuum chamber at high temperatures.

U.S. Pat. No. 6,244,936 of Kao et al entitled "Method and device for Reducing Semiconductor Defects Caused by Wafer Clamping" describes reducing defects in semiconductor wafers caused by a wafer clamp ring by polishing the surfaces of the clamp ring that engage and apply clamping force to the wafer. A polishing tool includes a circular plate supported on the stationary base. A layer or pad of polishing material, such as silicon carbide diamond, is deposited over the plate. The clamp ring is placed on the plate such that clamping surfaces of the ring engage the polishing material on the plate, and the ring is rotated to effect polishing of the clamping surfaces.

U.S. Pat. No. 6,523,426 of Vincent et al. entitled "Water Quality Measuring Apparatus with a Sensing Wafer Clamped Between Two O-Rings" describes a square wafer which measures the quality of water by detecting electroactive elements or compounds present in a solution, e.g. dissolved oxygen, pH, temperature, and chlorine and ammonia levels. The wafer is located between O-Rings on the top and bottom sides thereof so that the wafer is exposed to substantially equal pressure on both sides. Central portions of the wafer are exposed to equal amounts of atmospheric pressure and remaining peripheral portions of the wafer are exposed to equal amounts of water pressure.

SUMMARY OF INVENTION

The present invention makes it possible to enhance the apparatus and method for performance of a measurement as described by the copending Lu patent application. The present invention is applicable to semiconductor wafer wet processes such as electroplating, cleaning, etching, etc., where one side of a semiconductor wafer is wet and the other side of the semiconductor wafer is dry.

An advantage of the present invention is the fact that Z-axis direction forces applied to a DUT are cancelled. The present invention differs from the teachings of the Sherstinsky patent in that it provides dual contiguous seals along the entire wafer edge, and is designed to provide uniform, equal and opposite Z-axis forces at every point where the seals contact the edge of the DUT.

In comparison with U.S. Pat. No. 6,569,302 of Steinrücke, a primary element of the present invention is the strict adherence to perfectly aligned and identical seals to net zero Z-axis direction force.

An important feature of the present invention is that a pool of water is to be in contact with an upwardly facing surface of a workpiece, e.g. a semiconductor wafer, whereas a downwardly facing surface of the workpiece is protected by an isolated air pocket. There is the problem that a resultant differential force is created by a pool of water and an air pocket. We have found that it is necessary to compensate for that differential force. In accordance with the present invention, compensation for the differential force is provided by a net zero Z-axis wafer seal force differential, which serves to protect against stresses tending to break wafers. The net force on the surface of the upper gasket includes the weight of the fluid above it. There is an opposing seal provided by the lower gasket, which offsets the net force on the DUT itself, even though the seal and processing force are applied expressly to the top side of the DUT. The compression of the upper and lower gaskets, which is necessary to effect the fluid-tight isolation required for one side of the DUT, is cancelled out from the top to the bottom of the DUT along the wafer edge thereof by the opposing seal surfaces of the upper and lower gaskets which are designed to provide a resultant zero net force on the wafer. Thus, the force of the fluid plus the that of the seal compression on the sampling side of the wafer is equal to and opposed by the seal force on the non-sample side and completely offset by virtue of the direct alignment of the wafer seals to each other. Thus, the present invention accommodates both forces and indeed all forces (subject to reasonable limitation) to provide a net zero force differential on the surfaces of the DUT.

The present invention provides isolation of the water used in testing the DUT from one side thereof by employing a liquid seal.

As contrasted with Vincent et al. where the wafer is a sensing device and where the isolated area is limited to a portion of a wafer which is used to perform an electrical measurement on a water sample, the present invention performs in manner which is the opposite of Vincent in that it performs a measurement upon features of the wafer in contact with an acoustic transmission fluid rather than testing for electroactive elements or compounds present in a water sample.

Another advantage of the present invention is that it permits a wide operating zone nearly as wide as the DUT.

As described in the Lu U.S. patent application Ser. No. 11/495,243, the benefits of resolution of the features of a DUT that are available by performing this measurement with the sample are substantial.

A first feature of this invention is the ability to provide a water-tight seal to the workpiece, which is a semiconductor wafer, while applying symmetrical, i.e. equal and opposite, forces on the top and bottom surfaces of the wafer at the same radial location, thus nullifying the net force tending to bend the wafer thereby eliminating any potential of breakage.

A second feature of this invention is the ability to use a minimum of transmission medium, e.g. water.

A third feature of this invention is the provision of a Z-force means separate from the sealing means which insures preservation of the integrity of the sealing means.

The invention and objects and features thereof will be more readily apparent from the following detailed description and appended claims when taken with the drawings.

GLOSSARY

| Cam: | A rotating or sliding piece that in a mechanical linkage used in transforming rotary motion into linear motion or vice versa |
|---|---|
| Cam-ramp | A ramp along which a sliding cam slides |
| Sliding cam | A cam formed on a ring turning on its axis which drives the ring in a linear direction as the sliding cam slides along an anchored cam-ramp |

GLOSSARY -continued

| Elastomer | An elastic material that resembles rubber in that it resumes its original shape after removal of a deforming force. |
|---|---|
| Rubber: | An elastic hydrocarbon polymer that naturally occurs as a milky colloidal suspension or latex, in the sap of some plants. It can also be synthesized. |

BRIEF DESCRIPTION OF THE DRAWINGS

The foregoing and other aspects and advantages of this invention are explained and described below with reference to the accompanying drawings, in which:

FIGS. 1A and 1B are schematic drawings of a testing device comprising a C-SAM acoustic microscope and a fixture in accordance with this invention for use in testing a Device Under Test (DUT) such as a silicon semiconductor wafer.

FIG. 2A is an enlarged view of some elements of the device of FIG. 1A.

FIG. 2B is an enlarged view of a cylindrical guide pin provided to assure that the device under test (DUT), an upper sealing ring and a slip ring are properly aligned in the testing device shown in FIGS. 1A and 2A with the cylindrical guide pin aligned for insertion into a notch in the fixture of the testing device.

FIG. 3 is a fragmentary sectional elevation of the testing device of FIG. 1B showing the rotatable pressure plate of FIG. 1B and the cylindrical guide pin of FIG. 1B and FIG. 2B inserted through the fixture base into the fixture of FIG. 2A.

FIG. 4A is a side view of an L-shaped retainer shown in FIG. 1B, a horizontal retainer head of the fixture of FIG. 3, a vertical leg, a wedge shaped, fixed location ramp plus a phantom showing of a cylindrical guide pin and a hole.

FIG. 4B is a front view of the L-shaped retainer of FIG. 4A showing the vertical leg, the wedge shaped, fixed location ramp plus the hole which is shown in phantom.

FIG. 5A is a left sectional view of the horizontal retainer head of FIG. 4B assembled with the fixture base of FIG. 3 by a bolt.

FIG. 5B is a right sectional view of the horizontal retainer head of FIG. 4B assembled with the fixture base of FIG. 3 by a bolt.

FIG. 7A shows a plan view of a fragment of the rotatable pressure plate of FIGS. 1B, 3, 6A and 6B and the retainer head of FIG. 3.

FIG. 7B is an elevational view of a fragment of the rotatable pressure plate of FIG. 7A and the retainer head with the rotatable pressure plate in the closed position, with the sliding cam being pressed downwardly by the fixed location ramp of the retainer head.

Figures 6A, 6B:
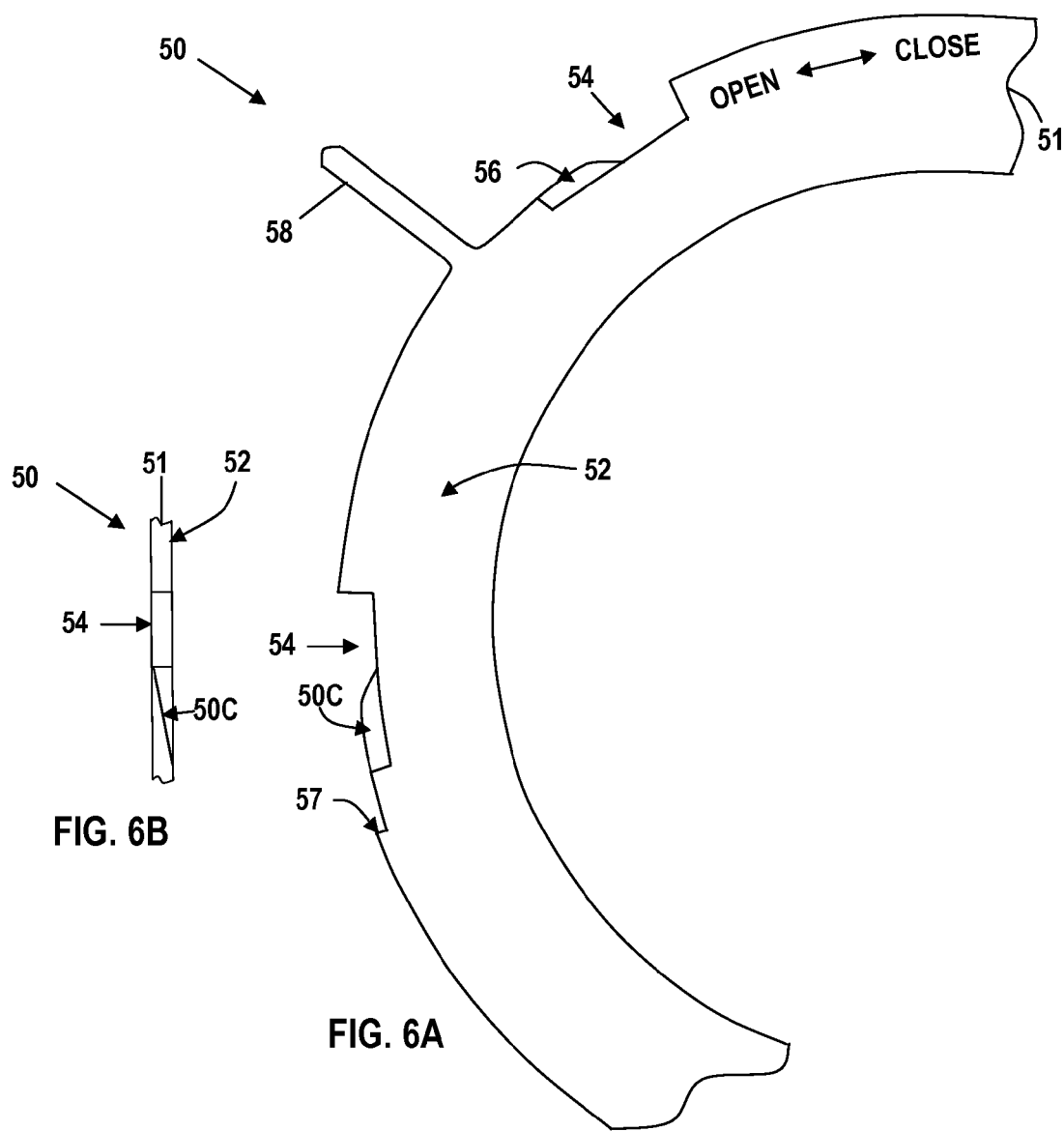
FIG. 6A shows a plan view of a fragment of the rotatable pressure plate of FIG. 1B.
FIG. 6B is an elevational view of a fragment of the rotatable pressure plate of FIG. 6A, which shows the angle of a sliding cam employed to press against the fixed location ramp of a retainer head.

The following detailed description explains the preferred embodiments of the invention, together with advantages and features, by way of example, with reference to the drawings.

DETAILED DESCRIPTION OF THE PREFERRED EMBODIMENT

FIGS. 1A and 1B are schematic drawings of a C-SAM testing device 10 comprising a C-SAM acoustic microscope in accordance with this invention for use in testing a Device Under Test (DUT) 11 such as a silicon semiconductor wafer. FIG. 1A is an elevational sectional view of the C-SAM testing device 10 taken along line A-A' in FIG. 1B. FIG. 1B is a plan view of the C-SAM testing device 10 of FIG. 1A. The C-SAM testing device 10 of FIG. 1A, which is used to test the integrity of features of the DUT 11, is supported by a fixture base 20.

As shown in FIG. 1A, the C-SAM testing device 10 includes a barrier structure comprising components which form a dam 12 adapted to hold a pool of acoustic transmission fluid 60 (such as water) on the planar, back surface B of the DUT 11, i.e. a silicon semiconductor wafer, thus enabling a C-SAM measurement of the type described in the copending Lu patent application, with a minimum amount of water and minimum associated setup and cleanup time. The dam 12, preferably about 3 mm deep, surrounds the back surface B of the DUT 11 and permits submersion of the lower end of the C-SAM transducer 70, which is necessary for proper measurement of parameters of the DUT 11. The back surface B of the DUT 11 faces upwardly. The front surface F of the DUT 11 faces downwardly towards the fixture base 20 above a space S formed above the hollow top surface 20H of the fixture base 20. The space S is located below the front surface F and inside the inner edge of a lower sealing ring 20R formed on the top surface of the fixture base 20.

The barrier structure surrounding the dam 12 is supported by the fixture base 20 which includes an elevated, lower sealing ring 20R formed surrounding the space S on the periphery of the central portion on the top surface of the fixture base 20. An annular dove tailed groove 20G, which is formed centered in the top surface of the lower sealing ring 20R, houses an impervious, concentric, elastic, lower O-ring gasket 23 which can be pressed into water tight contact with the front (lower) surface F of the DUT 11. A solid water tight, annular, upper sealing ring 26, which is positioned above the DUT 11 includes a dove tailed groove 26G shown in FIG. 2A which houses an impervious, elastic, upper O-ring gasket 29. The O-ring, gaskets 23 and 29, which are impervious and elastic may be composed of an elastomer, rubber or the like and are shown to be of equal diameter and are shown to be concentric and coaxial. An annular slip-ring 28 is rotatably secured to top of the upper sealing ring 26 and is coaxial therewith and has substantially equal inner and outer diameters.

FIG. 1B shows the plan view of the C-SAM testing device 10 with the fixture base 20 carrying six L-shaped retainers 40 which provide forces required to seal the interstices in the barrier by pressing down on the top surface of a low-friction, rotatable pressure plate 50 which is turned on its axis by a handle 58 to apply downward pressure on the annular slip-ring 28. The dam 12 is shown with the water 60 therein inside the inner perimeter of the pressure plate 50. The C-SAM transducer 70 is shown inserted into the water 60.

Referring again to FIG. 1A, each retainer 40 has a head 40H formed with a fixed location ramp 40R on the lower surface of the distal end of the retainer head 40H. The fixed location ramps 40R are wedge-shaped. A low-friction, rotatable pressure plate 50 which rests on the top surface of the slip-ring 28, includes sliding cams 50C on the top surface thereof. The slip ring 28 engages the low friction contact bearings 26B projecting from the top surface of the upper sealing ring 26. As an alternative, rollers can replace the contact bearings 26B. The application of a Z-axis force for sealing the dam 12 is provided by the rotatable pressure plate 50. The rotatable pressure plate 50 rotates about the edge of the DUT 11 and engages the fixed location ramps 40R that press down uniformly upon the slip ring 28 on top of the upper sealing ring 26 about the edge of the DUT 11. That is to say that when the rotatable pressure plate 50 rotates on its axis into a closed position the sliding cams 50C are pressed down by pressure exerted by the fixed location ramps 40R, as shown in FIGS. 7A and 7B. In that case, the rotatable pressure plate 50 exerts a downward Z-axis force upon the slip-ring 28. The upper O-ring gasket 29 is pressed down upon the back surface B of the DUT 11 thereby providing a seal as it is pressed into water tight contact with the back (upper) surface B of the DUT 11. The DUT 11 presses down on the lower O-ring gasket 23 which seals the space S above the hollow 20H in the top surface of the fixture base 20 and inside the lower O-ring gasket 23 which is impervious and elastic. It should be noted that when the direction of rotation of the rotatable pressure plate 50 reverses, i.e. rotates on its axis into a open position, the pressure exerted by the fixed location ramps 40R is released and the seals are unsealed. The sealing elements of the testing device 10 prevents localization of the Z-force, and permits uniform application of the compression force across the DUT 11.

As shown in FIG. 1A, the back surface B of the DUT 11 is completely immersed in the acoustic transmission fluid 60. The scanning C-SAM transducer 70 is shown above the wafer 14 with its lower end proximate to the back of the DUT 11 to couple acoustic energy to the back surface B of the DUT 11 to provide a C-SAM scan of the DUT 11. For example, the front surface F of the DUT 11 preferably includes features (not shown for convenience of illustration) such as multiple C4 solder bumps bonded to multiple BLM pads in the sealed space S located below the front F of the DUT 11. The front F of the DUT is isolated in the space S and thus it is protected from the acoustic transmission fluid 60.

Referring again to FIG. 1A, several elements of the testing device 10 are shown with the DUT 11 installed therein. The C-SAM testing device 10 includes a cylindrical fixture base 20 with a vertical axis (Z-axis) of the cylindrical body; an annular, and a lower sealing ring 20R formed in the upper surface thereof. The annular, lower sealing ring 20R surrounds a hollow 20H formed in the upper surface of the fixture base 20. The lower sealing ring 20R is concentric with the upper sealing ring 26. The lower sealing ring 20R houses an annular, concentric, lower impervious, elastic O-ring gasket 23 in an annular dove tailed groove (20G in FIG. 2A). The DUT 11 is shown supported by the annular, lower O-ring gasket 23 which is impervious and elastic is only partially compressed, leaving a space between the lower sealing ring 20R and the front surface F of the DUT 11.

There are several cylindrical guide pins 25 provided to assure that the DUT 1, the upper sealing ring 26 and the slip ring 28 are properly aligned. The slip ring guide pins 25 are adapted to contact the DUT 11 and the upper sealing ring 26 whereas the slip ring 28 is aligned because it is connected to the upper sealing ring 26. The guide pins 25 fit into alignment holes 24 in the fixture base 20. The guide pins 25 have tapered upper and lower ends so that as the guide pins 25 are inserted into the alignment holes 24 in the fixture base 20 the tapered upper ends of the guide pins 25 will gently move the DUT 11, the annular, upper sealing ring 26 and the annular slip ring 28 into a position centered in the testing device 10. Accordingly, the pins 25 are shown in contact with the peripheries of the upper sealing ring 26 and the DUT 11 to provide accurate alignment thereof. Two guide pins 25 are shown in FIG. 1A inserted into corresponding of cylindrical alignment holes 24.

The annular, upper sealing ring 26 is aligned, above the lower sealing ring 20R with the DUT 11 located therebetween. The upper sealing ring 26 has an annular dove tailed groove (28G in FIG. 2A) in the upper surface thereof which houses the upper O-ring gasket 29 which rests upon the top surface of the periphery of the wafer comprising the DUT 11. A slip ring 28, which is composed of a material such as nylon, includes an annular notch (28P in FIG. 2A) on the bottom surface thereof inserted into the annular, dove tailed groove 28G in the top surface of the upper sealing ring 26. With the annular notch 28P inserted into the annular dove tailed groove 26G, the slip ring 28 is free to rotate about the vertical, cylindrical axis of the fixture base 20, above the upper sealing ring 26. A rotatable pressure plate 50 with a handle 58, which lies above the slip ring 28, is free to rotate on the surface thereof. The rotatable pressure plate 50, the upper sealing ring 26, the upper O-ring gasket 29, the lower sealing ring 20R and the lower O-ring gasket 23 are all concentric with the Z-axis of the fixture base 20. When the rotatable pressure plate 50 is turned with the handle 58, the O-ring gaskets 23 and 29 are compressed with the DUT 11 between them, thereby sealing the dam 12 and the space S.

Each of the six L-shaped retainers 40 has a vertical leg extending up from the periphery of the top surface of the fixture base 20 and a horizontal retainer head 40H extending radially towards the Z-axis of the fixture base 20. The bottom of the vertical leg 40V of each retainer 40 is secured to the periphery of the fixture base 20 by a threaded screw 30 which extends through a hole 31 up into a threaded screw hole 32 in the bottom of the retainer 40. The bottom edges of the distal ends of the retainer heads 40H have wedge shaped, fixed location ramps 40R formed on the lower surfaces thereof.

FIG. 4A is a side view of an L-shaped retainer shown in FIG. 1B, a horizontal retainer head of the fixture of FIG. 3, a vertical leg, a wedge shaped, fixed location ramp plus a phantom showing of a cylindrical guide pin and a hole.

FIG. 4B is a front view of the L-shaped retainer of FIG. 4A showing the vertical leg, the wedge shaped, fixed location ramp plus the hole which is shown in phantom.

FIG. 5A is a left sectional view of the horizontal retainer head of FIG. 4B assembled with the fixture base of FIG. 3 by a bolt.

FIG. 5B is a right sectional view of the horizontal retainer head of FIG. 4B assembled with the fixture base of FIG. 3 by a bolt.

FIG. 6A shows a plan view of a fragment of the rotatable pressure plate 50. The rotatable pressure plate 50 is shown with a pressure plate ring 51, a top surface 52, a notch 54, sliding cam 50C, stop 57, and handle 58. The notch 54 and the stop 57 are formed in the outer edge of the pressure plate ring 51.

FIG. 6B is an elevational view of a fragment of the rotatable pressure plate 50 which shows the angle of the sliding cam 50C which is employed to press against the fixed location ramp 40R of a retainer head 40H.

FIG. 7A shows a plan view of a fragment of the rotatable pressure plate 50 and a retainer head 40H. The rotatable pressure plate 50 is shown with a pressure plate ring 51, a top surface 52, a notch 54, sliding cam 50C, and stop 57. The notch 54 and the stop 57 are formed in the outer edge of the pressure plate ring 51. The retainer head 40H is shown with the top ends of threaded screws 30 shown in phantom. The rotatable pressure plate 50 is shown in the open position.

FIG. 7B is an elevational view of a fragment of rotatable pressure plate 50 and the retainer head 40H with the rotatable pressure plate 50 in the closed position, with the sliding cam 50C being pressed downwardly by the fixed location ramp 40R of the retainer head 40H.

When the rotatable pressure plate 50 is turned by the handle 58 from the open position to the closed position, the sliding cams 50C are driven down to lower levels by the resistance force from the fixed location ramps 40R which are in fixed position. In other words, the fixed location ramps 40R press the sliding cams 50C down, thereby driving the rotatable pressure plate 50 downwardly with a vertical force in the Z-axis direction. The pressure plate 50 transmits the downward force in the Z-axis direction through the slip ring 28 and the upper sealing ring 26. The vertical force is sufficient to seal the interfaces between the upper O-ring 29, the DUT 11 and the lower O-ring 23. Thus the acoustic transmission fluid 60 is retained in the dam 12 by slip ring 28, the upper sealing ring 26 and the upper O-ring 29 above the DUT 11, and any leakage is excluded by the lower O-ring 23 from entering the space S below the DUT 11 and above the hollow top surface 20T of the fixture base 20.

FIG. 2A is an enlarged view of some elements of the testing device 10 of FIG. 1A. The retainer 40 is shown secured to the base 20 by the threaded screw 30. There is an open space 38 in the testing device 10 at the above alignment hole 24 in the base 20 and above the DUT 11 and the upper sealing ring 26, inside the retainer vertical legs 40V and below the horizontal retainer heads 40H and the rotatable pressure plate 50 and outside of the slip ring 28. FIG. 2A shows the lower, annular, dove tailed groove 20G in the top surface of the fixture base 20 which houses the lower O-ring 23, which provides a lower seal preventing gas or fluid from passing across the top surface of the lower sealing ring 20R. Above the DUT 11, the corresponding upper, annular, dove tailed groove 26G is shown formed in the upper sealing ring 26 which houses the upper O-ring gasket 29, which provides an upper seal preventing fluid from passing across the bottom surface of the upper sealing ring 26. The lower O-ring gasket 23 and the upper O-ring gasket 29, the upper, annular, dove tailed groove 26G, and the lower, annular, dove tailed groove 20R have substantially the same radii and are concentric so that the upper seal and the lower seal are aligned with each other with O-ring gasket 29 directly above the O-ring gasket 23. The O-ring gaskets 29 and 23 are shown to be in contact with the opposite back and front surfaces of the DUT 11 respectively.

There is a rotatable linkage between the annular, upper sealing ring 26 and annular slip ring 28 provided by an annular, dove tailed recess 26R in the top surface of the annular, upper sealing ring 26. The dove tailed recess 26R retains therein an annular flared plug 28P that is formed in the lower surface of the annular slip ring 28. The rotatable linkage permits rotation of the slip ring 28 about its vertical axis.

The slip ring 28 also engages the low friction, annular contact bearings 26B projecting from the top surface of the upper sealing ring 26 which reduce friction when the slip ring 28 turns beneath the low-friction, rotatable pressure plate 50 which rests on the top surface of the slip-ring 28. The rotatable pressure plate 50 includes sliding cams 50C on the top surface thereof which are shown in contact with a fixed location ramps 40R formed on the lower distal surface of the head 40H of the retainer 40, which forces the rotatable pressure plate 50 down along the Z-axis direction as the handle 58 turns the rotatable pressure plate 50, as will be explained in more detail below with reference to FIGS. 6A, 6B, 7A, and 7B.

FIG. 2B is an enlarged view of a cylindrical guide pin 25 provided to assure that the DUT 11, the upper sealing ring 16 and the slip ring 28 are properly aligned in the testing device shown in FIGS. 1A and 2A, with the cylindrical guide pin 25 aligned for insertion into a notch 24 in the fixture 20 of the testing device 10.

FIG. 3 is a fragmentary sectional elevation of the testing device 10 which shows the cylindrical, guide pin 25 of FIG. 2B inserted into the fixture 20 of FIG. 2A where it assures that the DUT 11, the upper sealing ring 26 and the slip ring 28 are properly aligned. The water 60 is illustrated as being retained by the dam 12 with the lower end of the C-SAM transducer 70 immersed in the water 60. There is an open space 38 in the testing device 10 above the alignment hole 24 and above the DUT 11 and the upper sealing ring 26, inside the retainer vertical legs 40V and below the horizontal retainer heads 40H and the rotatable pressure plate 50 and outside of the slip ring 28.

The dam 12 is formed surrounding the back surface B of the DUT 11. The dam is formed by the fixture base 20, the lower O-ring gasket 23 which is housed in a groove 20 in the fixture base 20, the upper sealing ring 26, the slip ring 28 and the rotatable pressure plate, and the upper O-ring gasket 29 which is housed in a groove in the upper sealing ring 26. The O-ring gasket 29 and the lower O-ring gasket 23 are the gasket 29 directly retained near the periphery of the back surface B of the DUT 11. When the rotatable pressure plate 50 is turned into the closed position by handle 58 and is driven down by camming action from the fixed location ramps 40R on the retainers 40, the pressure generated presses the O-ring gasket 29 down by upon the periphery of the back surface B of the DUT 11 and the DUT 11 presses down upon the lower O-ring gasket 23 to provide balanced Z-axis forces upon the DUT 11.

As stated above, back surface B of the DUT 11 is immersed in acoustic transmission fluid 60 and the front surface F thereof is sealed from contact with the acoustic transmission fluid 60. The C-SAM transducer 70 has an end thereof positioned in the acoustic transmission fluid 60 above the back surface B of the DUT 11. The C-SAM transducer 70 scans acoustic energy on the back surface B of the DUT 11 while isolated from the front surface F of the DUT 11 while it is sealed from the acoustic transmission fluid 60 and protected therefrom as described above.

As stated above, there has been a significant problem with total water immersion of a sample to be inspected by a C-SAM testing apparatus in water. The problem is that the acoustic transmission fluid 60 is a good transmitter of acoustic waves. Since the impedance difference between the acoustic transmission fluid 60 and BLM pads and bumps is very small, the location of the BLM boundary can not be clearly distinguished in the acoustic image. Since the space S is filled with air, which has a far lower density than that of the acoustic transmission fluid 60, the transmission of acoustic vibration energy therethrough is greatly reduced. Typical sizes of BLM pads and C4 bumps are about 25-500 μm, typically 50-150 μm. The acoustic frequency of the transducer 17 is from 15 MHz to 2 GHz, typically 50 MHz to 300 MHz. The DUT 11 can be a silicon wafer, a silicon wafer with BLM pads, a silicon wafer with BLM pads and solder, or a module where silicon chip is joined to a substrate through C4 arrays.

The fixture shown in FIG. 1A is designed to permit pooling or pooling of acoustic transmission fluid 60 on the surface of a workpiece comprising a DUT 11, thus enabling a C-SAM measurement of the type described in the copending Lu application (above) with a minimum amount (i.e. depth) of the acoustic transmission fluid 60 (and associated setup and cleanup time).

Critical features of the testing device 10 include provision of positive orientation of the DUT 11 by means of insertion of a set of wafer and slip ring guide pins 25 inserted into a set of alignment holes 24 in the fixture base 20 of testing device 10 and into set of retainer head cams 46 to provide alignment thereof. Also an upper sealing ring 26 is located above the periphery of the DUT 11 and lower sealing ring 102R is located below the periphery of the DUT 11. The upper sealing ring 26 and the lower sealing ring 26 contain dove tailed grooves 28G/26G respectively in which low durometer viton "sponge" O-ring gaskets 29/23 are housed. The lower sealing ring 20R is formed on the top surface of the fixture base 20. The grooves 108G/102G are located at fixed, prescribed and equal radial locations such that the application of sealing forces on the top and bottom of the DUT 11 are equal and offset, resulting in a net Z-axis direction force on the wafer, which makes the fixture essentially break-proof. Furthermore, the application of a vertical, Z-axis direction, force on the upper sealing ring 26 is provided via a low-friction, compression slip ring 108 located above the upper sealing ring 26. The compression slip ring 50 rotates about the edge of the DUT 11 and engages the set of retainer head cams 46 that press on the nylon compression slip ring 50 down uniformly on the top surface of the upper sealing ring 28 about the edge of the DUT 11, above the upper sealing ring 26 and lower sealing ring 20R. This prevents localized vertical, Z-axis direction force and permits uniform application of the compression force across the DUT 11. The compression slip ring 50 engages the upper sealing ring 26 with low friction contact points of either teflon or similar bearing materials.

The fixture materials are chosen from light weight materials to permit ease of handling, and include a fixture base 20, retainer head cams 46 and upper sealing ring 26 which are composed of a metal such as titanium (Ti) and a nylon rotatable pressure plate 50. By comparison to the fixture concepts of the subject application Ser. No. 11/495,243, the present invention precludes the use of a vacuum system, related seals, exposure to wafer implosion (due to stress cracking), and potential of having water "drawn" into the fixture at potential leak points due to use of negative pressure regions inside the fixture. The present invention also provides a secondary water-tight seal on the top-side of the edge of the DUT 11. The present invention is designed specifically to permit use of liquid on one side of the wafer, while keeping the opposing side water tight and separate from the water and exposed to environment of air or another preferred medium. This invention permits use of live product in the C-SAM system, and is compatible with non-destructive testing, which is an important aspect of this invention.

By comparison to the fixture concepts of the copending application Ser. No. 11/495,243 of Minhua Lu, the present invention precludes the use of a vacuum system, related seals, exposure to wafer implosion (due to stress cracking), and water "draw" into the fixture at potential leak points via use of negative pressure regions inside the fixture. The present invention also provides a secondary water-tight seal on the top-side of the wafer edge which is a feature omitted in the fixture drawings of the subject application. The present application is specifically designed to permit use of liquid on one side of the wafer, while keeping the opposing side water tight and in an air (or other preferred medium) environment.

Critical features of the subject invention include positive wafer orientation (via notch location pin), top and bottom compression seals (low durometer viton "sponge" gasket—minimal surface area), at fixed, prescribed and equal radial locations such that the application of seal forces on the top and bottom of the wafer are equal and offset, resulting in a net zero force, which makes the fixture essentially "break-proof".

A unique feature of this invention comprises the ability to provide a water-tight seal to the workpiece (wafer) while applying symmetrical forces on the top and bottom sides of the workpiece at the same radial location, thus nullifying the net force on the workpiece and eliminating any breakage potential.

Another unique feature of this invention comprises the ability to use a minimum of transmission medium (water), and the use of a sealing force means separate from the sealing means to ensure seal integrity of that means.

While this invention has been described in terms of the above specific embodiment(s), those skilled in the art will recognize that the invention can be practiced with modifications within the spirit and scope of the appended claims, i.e. that changes can be made in form and detail, without departing from the spirit and scope of the invention. Accordingly all such changes come within the purview of the present invention and the invention encompasses the subject matter of the following claims.

The invention claimed is:

1. Apparatus for Scanning Acoustic Microscopy (SAM) of a semiconductor device with an acoustic scanning probe comprising:
    said semiconductor device including a substrate having a first surface and a second surface and with acoustic transmission fluid retained in contact with said second surface by a dam;
    said apparatus comprising:
    a sealed lower space providing an environment surrounding said first surface comprising an atmosphere selected from a gas and a vacuum;
    an upper sealing ring structure formed above said second surface retaining an upper gasket in said upper sealing ring, with said upper gasket in contact with said second surface, with said upper sealing ring structure and said upper gasket forming said dam for retaining said acoustic transmission fluid above said second surface;
    a fixture base retaining a lower gasket in a lower sealing ring, with said lower gasket in contact with said first surface surrounding said first surface; and
    said acoustic scanning probe positioned confronting said second surface with said acoustic scanning probe extending into said acoustic transmission fluid which is retained in contact with said second surface by said dam.

2. The apparatus of claim 1 wherein said upper sealing ring and said lower sealing ring are concentric with substantially equal diameters and aligned with each other providing substantially equal opposing forces above and below said substrate.

3. Apparatus for Scanning Acoustic Microscopy (SAM) of a semiconductor device comprising:
    an acoustic probe;
    said semiconductor device including a substrate having a first surface and a second surface and with acoustic transmission fluid retained in contact with said second surface by a dam;
    said apparatus comprising: a sealed lower space providing an environment surrounding said first surface comprising an atmosphere selected from a gas and a vacuum;
    an upper sealing ring structure formed above said second surface retaining an upper gasket in an upper sealing ring, with the upper gasket in contact with said second surface, with said upper sealing ring structure and said upper gasket forming said dam for retaining said acoustic transmission fluid above said second surface;
    a fixture base retaining a lower gasket in a lower sealing ring, with said lower gasket in contact with said first surface aside surrounding said first surface;
    said acoustic probe positioned confronting said second surface extending into said acoustic transmission fluid which is retained in contact with said second surface;
    said upper ring sealing structure includes a rotatable pressure plate provided with sliding cams formed on an upper surface thereof; and
    a set of retainers secured to said fixture base with said retainers including retainer head ramps facing downwardly towards said sliding cams;
    whereby rotation of said pressure plate applies a clamping force upon said upper sealing structure for applying sealing force.

4. The apparatus of claim 1 wherein:
    a slip ring is formed above said upper sealing ring and is rotatably connected thereto; and
    a rotatable pressure plate is provided with sliding cams formed on an upper surface thereof.

5. The apparatus of claim 4 including:
    a set of retainers secured to said fixture base with said retainers including retainer head ramps facing downwardly towards said sliding cams;
    whereby rotation of said pressure plate applies a clamping force upon said upper sealing ring structure for applying sealing force.

6. The apparatus of claim 1 wherein said fixture base includes vertically aligned cylindrical notches with notch location pins inserted therein in contact with peripheral surfaces of said substrate and said upper ring structure.

7. The apparatus of claim 1 wherein said fixture base includes an annular groove housing said lower gasket and a central recess for providing said sealed lower space in combination with said lower gasket.

8. The apparatus of claim 1 wherein:
    said upper sealing ring including a groove for housing said upper gasket;
    a slip ring formed above said upper sealing ring and rotatably connected thereto; and
    a rotatable pressure plate provided with sliding cams formed on an upper surface thereof.

9. The apparatus of claim 8 including:
    a set of retainers secured to said fixture base with said retainers including retainer head ramps facing downwardly towards said sliding cams;
    whereby rotation of said pressure plate applies a clamping force upon said upper sealing ring structure for applying sealing force.

10. The apparatus of claim 9 wherein said fixture base includes an annular groove housing said lower gasket and a central recess for providing said sealed lower space in combination with said lower gasket.

11. A method for Scanning Acoustic Microscopy (SAM) of a semiconductor device with an acoustic scanning probe, said semiconductor device including a substrate having an first surface and a second surface with acoustic transmission fluid retained in contact with said second surface by a dam; said method comprising:
    providing a sealed lower space enclosing an environment surrounding said first surface comprising an atmosphere selected from a gas and a vacuum;
    providing an upper sealing ring structure above said second surface including an upper gasket in contact with said second surface, with said upper sealing ring structure and said upper gasket forming said dam for retaining said acoustic transmission fluid above said second surface,
    providing a fixture base retaining a lower gasket in a lower sealing ring with said lower gasket in contact with said first surface and surrounding said first surface; and
    scanning with said acoustic scanning probe positioned confronting said second surface of said semiconductor device and extending into said acoustic transmission fluid which is retained in contact with said second surface by said dam.

12. The method of claim 11 wherein said upper sealing ring and said lower sealing ring are concentric with substantially equal diameters and aligned with each other providing substantially equal opposing forces above and below said substrate.

13. The method of claim 11 including:
forming said upper ring structure includes a rotatable pressure plate with sliding cams formed on an upper surface thereof;
securing a set of retainers to said fixture base with said retainers including retainer head ramps facing downwardly towards said sliding cams;
whereby rotation of said pressure plate applies a clamping force upon said upper sealing structure for applying sealing force.

14. The method of claim 11 wherein:
forming said upper sealing structure including an upper sealing ring housing for said upper sealing ring;
forming a slip ring above said upper sealing ring housing and rotatably connected thereto; and
forming a rotatable pressure plate with sliding cams on an upper surface thereof.

15. The method of claim 14 including:
securing a set of retainers to said fixture base with said retainers including retainer head ramps facing downwardly towards said sliding cams;
whereby rotation of said pressure plate applies a clamping force upon said upper sealing structure for applying sealing force.

16. The method of claim 11 wherein said fixture base includes vertically aligned cylindrical notches with notch location pins inserted therein in contact with peripheral surfaces of said substrate and said upper ring structure.

17. The method of claim 11 wherein said fixture base includes an annular groove housing said lower sealing ring and a central recess for providing said sealed lower space enclosing said atmosphere selected from a gas and a vacuum in combination with said lower sealing ring.

18. The method of claim 11 wherein:
said upper sealing ring structure including a groove for housing said upper sealing ring;
forming a slip ring above said upper sealing ring and rotatably connected thereto; and
providing a rotatable pressure plate with sliding cams formed on an upper surface thereof.

19. The method of claim 18 including:
securing a set of retainers to said fixture base with said retainers including retainer head ramps facing downwardly towards said sliding cams;
whereby rotation of said pressure plate applies a clamping force upon said upper sealing structure for applying sealing force.

20. The method of claim 19 wherein said fixture base includes an annular groove housing said lower sealing ring and a central recess for providing said sealed lower space enclosing said atmosphere selected from a gas and a vacuum in combination with said lower sealing ring.

* * * * *